US011478550B2

(12) United States Patent
Fevre et al.

(10) Patent No.: US 11,478,550 B2
(45) Date of Patent: Oct. 25, 2022

(54) BIODEGRADABLE HYDROGEL AND METHODS FOR USE THEREOF (71) Applicants: International Business Machines Corporation, Armonk, NY (US); Institute of Bioengineering and Nanotechnology, Singapore (SG)

(72) Inventors: Mareva B. Fevre, San Jose, CA (US); James L. Hedrick, Pleasanton, CA (US); Ashlynn Lee, Singapore (SG); Nathaniel H. Park, San Jose, CA (US); Rudy J. Wojtecki, San Jose, CA (US); Yi Yan Yang, Singapore (SG); Zhi Xiang Voo, Singapore (SG)

(73) Assignees: INTERNATIONAL BUSINESS MACHINES CORPORATION, Armonk, NY (US); INSTITUTE OF BIOENGINEERING AND NANOTECHNOLOGY, The Nanos (SG)

( * ) Notice: Subject to any disclaimer, the term of this patent is extended or adjusted under 35 U.S.C. 154(b) by 827 days.

(21) Appl. No.: 16/198,556

(22) Filed: Nov. 21, 2018

(65) Prior Publication Data
US 2020/0155686 A1 May 21, 2020

(51) Int. Cl.
| *A61K 31/69* | (2006.01) |
| *A61K 47/34* | (2017.01) |
| *A61K 9/107* | (2006.01) |
| *B01J 13/10* | (2006.01) |
| *C08G 64/18* | (2006.01) |
| *C08L 69/00* | (2006.01) |
| *C08G 64/02* | (2006.01) |
| *C08G 81/00* | (2006.01) |
| *C08G 64/42* | (2006.01) |
| *C08G 65/337* | (2006.01) |
| *C08L 71/02* | (2006.01) |

(52) U.S. Cl.
CPC .............. *A61K 47/34* (2013.01); *A61K 9/107* (2013.01); *A61K 31/69* (2013.01); *B01J 13/10* (2013.01); *C08G 64/183* (2013.01); *C08G 64/42* (2013.01); *C08G 65/337* (2013.01); *C08G 81/00* (2013.01); *C08L 69/00* (2013.01); *C08L 71/02* (2013.01); *C08L 2203/02* (2013.01); *C08L 2205/025* (2013.01)

(58) Field of Classification Search
CPC ........ A61K 47/34; A61K 9/107; A61K 31/69; B01J 13/10; C08G 64/183; C08G 64/42; C08G 65/337; C08G 81/00; C08G 69/00; C08G 71/02; C08G 2203/02; C08G 2205/025; C08G 64/0241; C08G 64/025; C08G 64/0275; C08G 64/305; C08G 65/3317; C08G 65/3326; C08G 65/333; C08G 65/3348
See application file for complete search history.

(56) References Cited

PUBLICATIONS

Yu, Bing, Weizheng Fan, and Yue Zhao. "Gelation of Triblock Copolymers in Aqueous Solution through CO2-Triggered Electrostatic Interaction." Macromolecular Chemistry and Physics 218.17 (2017): 1700146. (Year: 2017).*
Lee, Ashlynn LZ, et al. "Injectable coacervate hydrogel for delivery of anticancer drug-loaded nanoparticles in vivo." ACS applied materials & interfaces 10.16 (2018): 13274-13282. (Year: 2018).*
Aguirre-Chagala, Yanet E., et al. "Phenylboronic acid-installed polycarbonates for the pH-dependent release of diol-containing molecules." ACS Macro Letters 3.12 (2014): 1249-1253. (Year: 2014).*
Ono, Robert J., et al. "Biodegradable Block Copolyelectrolyte Hydrogels for Tunable Release of Therapeutics and Topical Antimicrobial Skin Treatment." ACS Macro Letters 4.9 (2015): 886-891. (Year: 2015).*
Roy, Debashish, Jennifer N. Cambre, and Brent S. Sumerlin. "Future perspectives and recent advances in stimuli-responsive materials." Progress in Polymer Science 35.1-2 (2010): 278-301. (Year: 2010).*
Stuart, Martien A. Cohen, et al. "Assembly of polyelectrolyte-containing block copolymers in aqueous media." Current opinion in colloid & interface science 10.1-2 (2005): 30-36. (Year: 2005).*

* cited by examiner

*Primary Examiner* — Abigail Vanhorn
(74) *Attorney, Agent, or Firm* — Amin, Turocy & Watson, LLP (57) ABSTRACT

The subject matter of this invention relates to hydrogel compositions and, more particularly, to hydrogel compositions comprising block copolymers (BCPs) capable of self-assembly into nanoparticles for the delivery and controlled release of therapeutic cargos.

10 Claims, 5 Drawing Sheets

BIODEGRADABLE HYDROGEL AND METHODS FOR USE THEREOF

TECHNICAL FIELD

The subject matter of this invention relates to hydrogel compositions and, more particularly, to hydrogel compositions comprising block copolymers (BCPs) capable of self-assembly into nanoparticles for the delivery and controlled release of therapeutic cargos.

BACKGROUND

Block copolymers (BCPs) comprise two or more covalently-linked homopolymer subunits, each homopolymer subunit made up of polymerized monomers. Block copolymers made up of two homopolymer subunits are referred to as diblock copolymers, those with three homopolymer subunits are referred to as triblock copolymers, etc. In any BCP, the junction of homopolymer units may, in some cases, include a junction block, a non-repeating subunit.

BCPs may be formed using any number of techniques, including, for example, atom transfer free radical polymerization (ATRP), reversible addition fragmentation chain transfer (RAFT), and ring-opening metathesis polymerization (ROMP), as will be appreciated by one skilled in the art.

Although BCPs have been used in many contexts, of more recent interest is their use in the encapsulation and delivery of other molecules, including drugs. When used in such methods, an amphiphilic BCP is made to form a micelle, with the molecule to be delivered contained therein.

Polymer-based micelles provide several advantages over other nano-carriers, such as liposomes. Among these advantages are their small size (10-100 nm), a reasonably low polydisperity index, and the ability to combine a hydrophobic core and a hydrophilic shell. The hydrophobic core facilitates the loading of hydrophobic cargo, including hydrophobic drugs, while the hydrophilic shell provides improved stability in aqueous environments.

Body tissues and cellular components have varying pH values. Blood and normal extracellular matrix, for example, have a pH of about 7.4, while the pH of a tumor extracellular environment is about 6.5, attributable to a lower oxygen supply in the intercellular environment. The pH in endosomes and lysosomes is even lower (5.0-5.5).

Some polymer-based micelles have been constructed to target tumor tissues and tumor cells based on this difference in pH. However, these have suffered from various deficiencies, including poor target specificity and lethargic drug release at the target site. In addition, it has been discovered that such micelles must be within a relatively narrow size range to be effective in most applications. Particles larger than about 100 nm, for example, have been found not to efficiently penetrate the extensive vasculature of most tumors. At the same time, micelles less than about 10 nm in size are below the renal threshold and are rapidly flushed from tumor sites and excreted.

SUMMARY

Aspects of the disclosure provide hydrogels comprising BCPs and methods for their manufacture and use.

A first aspect provides a hydrogel composition comprising: a first ABA triblock copolymer having negatively charged A blocks; and a second ABA triblock copolymer having positively charged A blocks.

A second aspect provides a hydrogel composition comprising: an AB diblock copolymer having a negatively charged A block; and an ABA triblock copolymer having positively charged A blocks.

A third aspect provides a micellar particle comprising: a hydrogel composition comprising: a first ABA triblock copolymer having negatively charged A blocks; and a second ABA triblock copolymer having positively charged A blocks; and at least one agent for delivery within the hydrogel composition.

A fourth aspect provides a micellar particle comprising: a hydrogel composition comprising: a first ABA triblock copolymer having negatively charged A blocks; and a second ABA triblock copolymer having positively charged A blocks; and at least one agent for delivery within the hydrogel composition.

A fifth aspect provides a method of treating, in an individual in need of such treatment, a disease or disorder amenable to treatment with a therapeutic agent, the method comprising: administering to the individual a hydrogel composition selected from a group consisting of: (a) a hydrogel composition comprising: a first ABA triblock copolymer having negatively charged A blocks; a second ABA triblock copolymer having positively charged A blocks; and at least one agent for delivery within the hydrogel composition; and (b) a hydrogel composition comprising: an AB diblock copolymer having a negatively charged A block; and a third ABA triblock copolymer having positively charged A block; and at least one agent for delivery within the hydrogel composition.

BRIEF DESCRIPTION OF THE DRAWINGS

These and other features of this invention will be more readily understood from the following detailed description of the various aspects of the invention taken in conjunction with the accompanying drawings in which.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Multiple myeloma (MM) is the second most prevalent blood cancer after non-Hodgkin lymphoma in the United States, accounting for 1.8% new cancer cases and 2.1% cancer deaths in 2016. Currently, several therapies are available for managing myeloma, including radiotherapy, surgery, chemotherapy and stem cell/bone marrow transplantation. Chemotherapy is one of the main treatments used to control myeloma and typical treatment regimens for multiple myeloma include combinations of various drugs such as melphalan, bortezomib, thalidomide, lenalidomide and corticosteroids.

Amongst the anti-cancer agents that are effective against MM, bortezomib (BTZ) stands as being the first proteasome inhibitor to be approved by the U.S. Food and Drug Administration (FDA) and the European Agency for the Evaluation of Medicinal Products for the treatment of refractory or relapsed MM. BTZ has demonstrated significant anti-tumor activity as a single agent in refractory and/or relapsed MM compared to dexamethasone, with a significantly longer survival (1-year overall survival rate of 80% vs. 66%) and a 78% longer median time to progression.

Like most anti-cancer drugs, BTZ causes a number of adverse side effects. It is administered via standard intravenous bolus or subcutaneous injection. A phase I study comparing the pharmacokinetics and pharmacodynamics of the two administration methods showed that the mean maximum plasma concentration of BTZ was lower, and took longer time to reach following subcutaneous administration (2 h vs. 3 min), but overall, systemic BTZ exposure was similar between the two routes. As such, delivering BTZ via localized administration within a micelle/hydrogel composite matrix that serves as both a drug reservoir and diffusion barrier may allow for sustained drug release and prolonged blood circulation, hence improving anti-tumor efficacy and lowering side effects.

According to one embodiment of the invention, Applicant synthesized an amphiphilic diblock copolymer of poly(ethylene glycol) (PEG) and catechol-functionalized polycarbonate via organocatalytic ring-opening polymerization (OROP) of phenylboronic acid (PBA)-functionalized cyclic carbonate with PEG serving as the macroinitiator. PBA-functionalized polycarbonate was chosen as it is biodegradable, and the degraded products are non-toxic.

BTZ was encapsulated into micelles using the polymer via a pH-sensitive boronate ester bond formed between boronic acid in BTZ and catechol. The boronate ester bond is stable when the micelles circulate in the blood but dissociates in the endolysosomes (pH 4.5-6.0) following endocytosis. This pH-sensitivity may prevent premature drug release in the blood stream while increasing bioavailability inside cancer cells.

Similarly, according to another embodiment of the invention, ABA triblock copolymers of PEG (B block) and PBA-functionalized polycarbonate (A block) were synthesized via OROP to form hydrogels for sustained delivery of the BTZ-loaded micelles. The empty p-orbital of boron contributes to its overall Lewis acidity and can be facially interconverted from $sp^2$ to $sp^3$ hybridization in the presence of Lewis bases, e.g., in an aqueous medium where water converts the neutral trigonal boron to an anionic tetrahedral geometric configuration. This unique property allows PBA to undergo a marked inversion in its original state of hydrophobicity, depending on its degree of acid dissociation. PBA retains hydrophobicity when uncharged and turns hydrophilic upon obtaining an anionic tetrahedral configuration at pH above pKa of PBA.

PBA-functionalized triblock copolymers can form hydrogels, depending on pH. PBA exists in equilibrium between the neutral and ionized boronic acid when pH of the aqueous media is approximately similar to its pKa. This mixture of uncharged and tetrahedral anionic forms intensifies the intermolecular hydrogen bonding, thus driving the gelation of the polymers.

To modulate mechanical strength for injectability, PBA-functionalized triblock copolymers were mixed with oppositely charged ABA triblock copolymers containing cationic A-blocks (e.g., guanidine- and thiouronium-functionalized polycarbonate) via coaservation, as coaservates are known to have lower moduli.

Ionic coacervation allows for the formation of moduli and rheological variant hydrogels via simple mixing at room temperature using low polymer concentrations. In addition, network defects or "dangling chain-ends" were deliberately introduced to improve processability by mixing of ABA triblock with AB diblock of phenylboronic acid moieties.

The BTZ-loaded micelles were incorporated into the hydrogel network to create a drug reservoir for localized and sustained delivery of the drug. The BTZ-loaded micelles/hydrogel composites were tested on mice bearing tumors induced by human MM.1S cells and investigated for anti-cancer efficacy.

A more detailed explanation of the invention, including illustrative examples, follows. The specific examples provided are merely illustrative of various aspects and embodiments of the invention. As will be recognized by one skilled in the art, other examples are possible and within the scope of the invention.

Co-Polymer Syntheses

HO-PEG-OH and Methyl-PEG (mPEG-OH) (Mn 10000 g·mol$^{-1}$, PDI 1.05 and 1.10, respectively) were purchased from Polymer Source™, lyophilized and transferred to a glove-box one day prior to use. 1,8-Diazabicyclo[5,4,0]undec-7-ene (DBU) was dried over $CaH_2$ overnight. Dried DBU was obtained after vacuum distillation, and transferred to a glove-box prior to use. BTZ was purchased from LC Laboratories (USA). All other chemicals were purchased from Sigma-Aldrich, and used as received unless stated otherwise. Human breast cancer cells SKBR3 and human multiple myeloma MM.1S were cultured in RPMI1640 medium supplemented with 10% fetal calf serum, 100 U/mL penicillin and 100 µg/mL streptomycin (HyClone, USA).

Synthesis of MTC-PPB Monomer

Briefly, in a dry two-neck 500 mL round bottom flask equipped with a stir bar, MTC-OH (3.08 g, 19.3 mmol) was first dissolved in dry tetrahydrofuran (THF, 50 mL) with 5-8 drops of dimethylformamide (DMF). Subsequently, oxalyl chloride (3.3 mL) was added in one shot (pure form), followed by an additional 20 mL of THF. The solution was stirred for 90 min, after which volatiles were dried under a strong flow of nitrogen to yield a pale yellow solid intermediate (5-chlorocarboxy-5-methyl-1,3-dioxan-2-one, MTC-Cl).

The solid was then subjected to heating at 60° C. for 2-3 min for the removal of residual solvent, and was re-dissolved in dry dichloromethane ($CH_2Cl_2$, 50 mL), followed by immersing the flask in an ice bath at 0° C. A mixture of 4 hydroxymethyl phenylboronic acid pinacol ester (4.19 g, 17.88 mmol) and pyridine (1.55 mL, 19.3 mmol) were dissolved in dry $CH_2Cl_2$ (50 mL), which was added dropwise to the flask over a duration of 30 min. The reaction mixture was then allowed to stir at room temperature (~22° C.) for an additional 2.5 h.

The reaction was quenched by addition of 50 mL of brine, and the organic solvent was collected. After removal of solvent, the crude product was purified by silica-gel flash column chromatography via a hexane-ethyl acetate solvent system (gradient elution up to 20% vol. ethyl acetate) followed by a solvent switch to dichloromethane-ethyl acetate (gradient elution up to 20% vol. ethyl acetate) to yield the protected phenylboronic acid-functionalized cyclic carbonate (MTC-PPB) monomer as a white solid.

The crude product was further purified by recrystallization. The solid was dissolved in 50 mL of diethyl ether and the residues were filtered. The filtrate was dried and subsequently dissolved in 2 ml of diethyl ether and ethyl acetate (1 mL each), followed by addition of 50 mL of hexane. The crystals are allowed to form at room temperature for 1 day, and are subsequently obtained by washing the crystals with cold hexane. $^1$H NMR (400 MHz, CDCl$_3$, 22° C.): δ7.83-7.32 (m, 4H, —C$_6$H$_4$B=), 5.22 (s, 2H, —CH$_2$C$_6$H$_4$-), 4.72-4.18 (m, 4H, —COOCH$_2$—), 1.34 (s, 12H, —OC(CH$_3$)$_4$CO—), 1.32 (m, 3H, —CH$_3$).

Synthesis of 2-hydroxyethyl 3,4-bis(benzyloxy)benzoate

The first step involves mixing of 3,4-dihydroxy benzoic acid (5 g, 32.44 mmol), benzyl bromide (15.41 mL, 129.76 mmol), and potassium carbonate (17.93 g, 129.73 mmol) in 100 mL of acetonitrile under refluxed for 18 h. The reaction solution was cooled to room temperature and the salts were filtered out. The solution was then concentrated down to 20 mL and diluted with 100 mL of hexanes. A solid was formed, and harvested by filtration. The solid was then recrystallized out of THF/hexanes to yield a pure product (7.88 g, 57.3% yield). $^1$H NMR (400 MHz, CDCl$_3$, 22° C.): δ7.70-7.68 (m, 2H, —COOCCH—), 7.47-7.28 (m, 15H, —CH$_2$C$_6$H$_5$), 6.96-6.93 (m, 1H, —COOCCHCCHC—), 5.34 (s, 2H, —COOCH$_2$C$_6$H$_5$), 5.25-5.21 (d, J=20 Hz, 4H, —C$_2$CO(CH$_2$C$_6$H$_5$)$_2$.

In the second step, protected 3,4-dihydroxy benzoic acid (4 g, 9.43 mmol) was suspended in ethylene glycol (50 mL), and the mixture was heated to 80° C. A catalytic amount of KOH (0.106 g, 1.86 mmol) was added and the mixture was left to react until all solids were dissolved (overnight or one day). The solution was precipitated into cold water (500 mL) and left to stir for several hours, during which a white solid was formed. The solid was obtained by filtration and rinsed with water, and subsequently lyophilized to remove the remaining water (2.81 g, 78.71% yield). $^1$H NMR (400 MHz, CDCl$_3$, 22° C.): δ7.69-7.66 (m, 2H, —COOCCH—), 7.45-7.28 (m, 10H, —CH$_2$C$_6$H$_5$), 6.97-6.95 (m, 1H, —COOCCHCCHC—), 5.26-5.23 (d, J=12 Hz, 4H, —C$_2$COCH$_2$C$_6$H$_5$), 4.45-4.43 (m, 2H, —COOCH$_2$CH$_2$—), 3.95 (s, 2H, —COOCH$_2$CH$_2$OH).

Synthesis of MTC-ProtCat Monomer

Briefly, MTC-Cl was dissolved in dry dichloromethane (CH$_2$Cl$_2$, 50 mL) in a dry two-neck 500 mL round bottom flask, which was then immersed in an ice bath at 0° C. A mixture of 2-hydroxyethyl 3,4-bis(benzyloxy)benzoate (4.19 g, 17.88 mmol) and triethylamine (1.77 mL, 19.3 mmol) were dissolved in dry CH$_2$Cl$_2$ (50 mL), and added dropwise to the flask over a duration of 30 min. The mixture was allowed to stir at room temperature (~22° C.) for an additional 2.5 h.

The reaction was quenched by addition of 50 mL of brine, and the organic solvent was collected. After removal of the solvent, the crude product was purified by silica-gel flash column chromatography via a dichloromethane-ethyl acetate solvent system (gradient elution up to 20% vol. ethyl acetate) to yield the protected catechol-functionalized cyclic carbonate (MTC-ProtCat) monomer as a white solid.

The crude product was further purified by recrystallization. The solid was dissolved in 2 mL of diethyl ether and ethyl acetate (1 mL each), followed by addition of 50 mL of hexane. The crystals are allowed to form at room temperature for 1 day, and are subsequently obtained by washing the crystals with cold hexane. $^1$H NMR (400 MHz, CDCl$_3$, 22° C.): δ7.65-7.63 (m, 2H, —COOCCH—), 7.46-7.28 (m, 10H, —CH$_2$C$_6$H$_5$), 6.98-6.96 (m, 1H, —COOCH$_2$CH—), 5.26-5.23 (d, J=12 Hz, 4H, —C$_2$COCH$_2$C$_6$H$_5$), 4.70-4.67 (m, 2H, —COOCH$_2$CH$_2$—), 4.54 (m, 4H, COOCH$_2$CC2-), 4.21-4.18 (s, 2H, —COOCH$_2$CH$_2$OH), 1.32 (s, 3H, —CH$_3$).

Synthesis of Phenylboronic Acid-Functionalized Polycarbonate Copolymers

Details of the metal-free organocatalytic ring-opening polymerization for synthesis of a phenylboronic acid-functionalized polycarbonate and PEG ABA triblock copolymer (P(Bor)$_5$-PEG-P(Bor)$_5$) of formula I is given as an example, wherein m is between 1 and 10 and PEG$_{10K}$ is 10 kDa poly(ethylene glycol).

(formula I)

In a glove-box, 0.556 g (0.056 mmol) of 10 kDa OH-PEG-OH initiator and 0.376 g (1 mmol) of MTC-PPB were charged in a 20 mL glass vial equipped with a stir bar. Dichloromethane was added and the monomer concentration was adjusted to 2 M. Once the initiator and monomer were completely dissolved, 8.3 µL (0.06 mmol) of DBU was added to initiate the polymerization. After 3.5 h of stirring at room temperature, the reaction was quenched with 30 mg of benzoic acid. Subsequently, the polymer intermediate was purified via precipitation twice in cold diethyl ether, and was dried on a vacuum line until a constant weight was achieved. $^1$H NMR (400 MHz, CDCl$_3$, 22° C.): δ7.81-7.28 (m, 40H, —C$_6$H$_4$B═), 5.19-5.11 (m, 20H, —CH$_2$C$_6$H$_4$—), 4.45-4.20 (m, 40H, —COOCH$_2$—), 3.84.-3.43 (m, 909H, —OCH$_2$CH$_2$— from 10 kDa PEG), 1.35-1.31 (m, 120H, —OC(CH$_3$)$_4$CO—), 1.26-1.16 (m, 30H, —CH$_3$).

The protected copolymer was then deprotected by dissolving in 14 mL of methanol and THF (1:1) and 10 equivalents (with respect to moles of protected phenylboronic pinacol pendant groups) of benzene-1,4-diboronic acid, and DOWEX® 50W-X2 acidic resins were added to a 50 mL round bottom flask containing the protected polymer. The flask was subsequently heated to 50° C. with overnight stirring. The solvents were then removed under vacuum and the deprotected polymer was dissolved in 10 mL of isopropanol and acetonitrile (1:1) and placed within a dialysis bag of 1000 MW cut-off. Dialysis was carried for the next 2 days at room temperature using 1:1 isopropanol and acetonitrile. Finally, the solvents were removed and the polymer was lyophilized to obtain an off-white product. $^1$H NMR (400 MHz, DMSO-$d_6$, 22° C.): δ8.08-8.00 (m, 40H, —B(OH)$_2$), 7.80-7.18 (m, 40H, —C$_6$H$_4$B═), 5.19-5.03 (m, 20H, —CH$_2$C$_6$H$_4$—), 4.37-4.04 (m, 40H, —COOCH$_2$—), 3.79-3.41 (m, 909H, —OCH$_2$CH$_2$— from 10 kDa PEG), 1.30-1.03 (m, 30H, —CH$_3$).

Phenylboronic acid-functionalized polycarbonate and PEG diblock copolymer (PEG-P(Bor)) was synthesized and worked up in similar fashion, with the exception of the initiator. In a glove-box, 0.22 g (0.022 mmol) of 10 kDa mPEG-OH initiator and 0.376 g (1 mmol) of MTC-PPB were charged in a 20 mL glass vial equipped with a stir bar. Subsequently, the synthetic protocols were carried out similarly to those for the synthesis of P(Bor)$_5$-PEG-P(Bor)$_5$.

Synthesis of Thiouronium-Functionalized Polycarbonate and PEG Triblock Copolymer In a nitrogen filled glovebox, a 20 mL glass vial was charged with azeotropically dried poly(ethylene glycol) (M$_n$=10000 Da; 1.50 g, 0.15 mmol, 1 equiv), MTC-OCH$_2$BnCl (0.538 g, 1.80 mmol, 12 equiv), TU (27 mg, 0.07 mmol), a Teflon-coated stir bar, and dry CH$_2$Cl$_2$ (2.0 mL). The contents of the vial were allowed to dissolve, and DBU (11 mg, 0.07 mmol) was added to start the polymerization. After stirring for 30 minutes at room temperature, an excess of benzoic acid (30 mg, 0.24 mmol) was added to quench the catalyst and stop the polymerization.

The crude reaction mixture was then precipitated into diethyl ether (40 mL). Three cycles of trituration, centrifugation, and decantation of the diethyl ether supernatant, followed by drying under reduced pressure, afforded the desired polymer (P(BnCl)-PEG-P(BnCl)) as a white solid (1.94 g, 95% yield). $^1$H NMR (400 MHz, CDCl$_3$): δ7.36-7.28 (br d, 40H, Ar—H), 5.12 (s, 20H, —OCH$_2$-BnCl), 4.55 (s, 20H, —CH$_2$–Cl) 4.26 (br, 40H, —OCOOCH$_2$— and —OCH$_2$CCH$_3$—), 3.64 (s, 909H, PEG —OCH$_2$CH$_2$—), 1.23 (s, 30H, —CH$_3$). GPC: Mn=22236, Mw=23592, Đ=1.06.

To a 20 mL glass vial was added polymer P(BnCl)-PEG-P(BnCl) (1.94 g, 1.8 mmol BnCl groups), thiourea (0.418 g, 5.5 mmol), and DMF (5 mL). The reaction mixture was stirred for 18 h at 40° C., transferred directly to a dialysis membrane (1000 Da molecular weight cut-off (MWCO)), and dialyzed against water for 18 h. Lyophilization afforded the desired polymer P(Th)-PEG-P(Th) as a white solid (1.88 g, 90% yield) of formula II, wherein x is between 1 and 10, n is 227, and TFA is trifluoroacetic acid.

(formula II)

$^1$H NMR (400 MHz, DMSO-d$_6$): 9.22 (br, 40H, —NH and —NH2), 7.44-7.30 (m, 40H, Ar—H), 5.11 (s, 20H, —O—CH$_2$—Ar), 4.50 (s, 20H, —CH$_2$—S—), 4.25 (m, 40H, —OCOOCH$_2$— and —OCH$_2$CCH$_3$—), 3.49 (s, 909H, PEG —OCH$_2$CH$_2$—), 1.18 (s, 30H, —CCH$_3$).

Synthesis of Protected Guanidinium- and Guanadinium-Functionalized Polycarbonate and PEG Triblock Copolymers Using a glove box, HO-PEG-OH was added to a reaction vial containing TU (18.5 mg, 0.05 mmol) and DBU (7.47 μL, 0.05 mmol) dissolved in dry DCM (1 mL) and left to stir for about 10 min. The mixture was subsequently charged with protected guanidinium-functionalized cyclic carbonate (MTC-OCH$_2$BnBocGu) (261 mg, 0.5 mmol) and left to stir at room temperature for an additional 30 min. At the end of the reaction, an excess of benzoic acid (10 mg, 0.08 mmol) was added to quench the catalyst.

The crude reaction mixture was then precipitated into diethyl ether (40 mL). Three cycles of trituration, centrifugation, and decantation of the diethyl ether supernatant, followed by drying under reduced pressure, afforded the desired polymer P(BocGu)$_5$-PEG-P(BocGu)$_5$ as a white solid (90% yield). $^1$H-NMR (400 MHz, CDCl$_3$, 22° C.):

δ11.54 (bs, 9H, NH), 8.66 (bs, 9H, NH), 7.30 (m, 36H, phenyl —CH), 5.13 (m, 18H, —CH$_2$—), 4.64 (m, 18H, —CH$_2$—), 4.27 (m, 36H, —CH$_2$—), 3.65 (m, 909H, PEG —CH$_2$—), 1.53-1.43 (m, 173H, Boc —CH$_3$), 1.27-1.21 (m, 24H, —CH$_3$).

For the post-polymerization removal of Boc groups, an acid-mediated deprotection strategy was adopted. In a 20-mL reaction vial, P(BocGu)$_5$-PEG-P(BocGu)$_5$ (700 mg) was dissolved in CH$_2$Cl$_2$ (9 mL) and trifluoroacetic acid (1 mL). The reaction mixture was sealed and stirred at room temperature for 18 h. After the removal of solvent in vacuo, a slightly yellow waxy solid was obtained as the deprotected guanidinium-functionalized polycarbonate in quantitative yields. The polymer was subsequently dissolved in water and lyophilized to yield a white transparent solid, P(Gu)$_5$-PEG-P(Gu)$_5$ of formula III, wherein m is between 1 and 10 and n is 227.

Complete deprotection was ascertained by $^1$H-NMR analysis. Yield: 87%; $^1$H-NMR (400 MHz, DMSO, 22° C.): δ8.18-7.92 (m, 9H, NH), 7.34 (m, 52H, phenyl —CH and NH), 5.12 (m, 19H, —CH$_2$—), 4.40-4.14 (m, 56H, —CH$_2$—), 3.51 (bs, 909H, PEG —CH$_2$—), 1.24-1.07 (m, 28H, —CH$_3$).

Synthesis of PEG-P(Cat)$_{13}$ Diblock Copolymer

In a glove-box, 0.33 g (0.033 mmol) of 10 kDa mPEG-OH initiator and 0.521 g (1 mmol) of MTC-ProtCat were charged in a 20 mL glass vial equipped with a stir bar. Dichloromethane was added and the monomer concentration was adjusted to 2 M. Once the initiator and monomer were completely dissolved, 9.0 µL (0.06 mmol) of DBU and 18.5 mg of TU co-catalyst were added to initiate the polymerization.

After 1 h of stirring at room temperature, the reaction was quenched with 30 mg of benzoic acid. Subsequently, the polymer intermediate was purified via precipitation twice in cold diethyl ether, and was dried on a vacuum line until a constant weight was achieved. $^1$H NMR (400 MHz, CDCl$_3$, 22° C.): δ7.67-7.27 (m, 156H, —C$_6$H$_5$ & —COOCCH$_2$—), 6.97-6.81 (m, 13H, —COOCH$_2$CH—), 5.32-5.00 (m, 52H, —COCH$_2$—), 4.57-4.32 (m, 52H, —OC$_2$H$_4$O—), 4.31-4.10 (m, 52H, —COOCH$_2$—), 3.89-3.42 (—OCH$_2$CH$_2$— from 10 kDa PEG), 3.38 (s, 3H, CH$_3$-PEG-), 1.29-1.04 (m, 39H, —CH$_3$).

The protected polymer was then deprotected by a hydrogenation process. It was first dissolved in 14 mL of methanol and THF (1:1), followed by addition of 2 spatulas of Pd/C into a 50 mL glass vial. The glass vial was placed under hydrogen at room temperature with overnight stirring. The polymer was harvested by filtration, and then dried under vacuum, dissolving the polymer in acetonitrile/isopropanol (1:1) solvent mixture and followed by reprecipitation in cold diethyl ether twice. Finally, the solvents were removed and the polymer was lyophilized to obtain an off-white product of formula IV, wherein m is between 1 and 10 and MPEG$_{10K}$ is 10 kDa methyl-poly(ethylene glycol).

(formula III)

(formula IV)

$^1$H NMR (400 MHz, DMSO$_d$, 22° C.): δ7.59-7.05 (m, 26H, —COOC$_2$H$_2$—), 6.79-6.74 (m, 13H, —COOCH$_2$CH—), 4.39-4.27 (m, 52H, —OC$_2$H$_4$O—), 4.23-4.06 (m, 52H, —COOCH$_2$—), 3.96-3.47 (—OCH$_2$CH$_2$— from 10 kDa PEG), 3.23 (s, 3H, CH$_3$-PEG-), 1.15-1.06 (m, 39H, —CH$_3$).

Hydrogel Properties

The critical aggregation concentrations (CACs) of the amphiphilic ABA-type triblock copolymers $P(Bor)_5$-PEG-P$(Bor)_5$ (formula I), $P(Th)_5$-PEG-P$(Th)_5$ (formula II), and $P(Gu)_5$-PEG-P$(Gu)_5$ (formula III) were determined to be 14, 66 and 490 mg/L, respectively, as shown in Table 1 below.

TABLE 1

| Polymer | CAC (mg/L) |
|---|---|
| $P(Bor)_5$-PEG-P$(Bor)_5$ | 14 |
| $P(Th)_5$-PEG-P$(Th)_5$ | 66 |
| $P(Gu)_5$-PEG-P$(Gu)_5$ | 490 |
| PEG-P$(Cat)_{12}$ | 21 |

Boronic acid-functionalized polymers exhibited greater propensity for micelle formation and this is attributed to the strong interactions between the boronic acid groups. The CAC value for $P(Th)_5$-PEG-P$(Th)_5$ is lower than that of $P(Gu)_5$-PEG-P$(Gu)_5$ due to the difference in hydrophobicity between the two polymers. The strong hydrogen bonding between boronic acid moieties in $P(Bor)_5$-PEG-P$(Bor)_5$ enabled it to form hydrogel at ≥10 wt. %. It is possible that the rheological properties of the hydrogel can significantly affect the drug release kinetics. Hence, other ABA-type triblock copolymers $P(Th)_5$-PEG-P$(Th)_5$ and $P(Gu)_5$-PEG-P$(Gu)_5$, capable of forming hydrogels through ionic coacervation, were incorporated to enable fine tuning of the viscoelastic behavior of the gels.

Table 2, below, shows rheological properties of hydrogels according to various embodiments of the invention. As can be seen, the gelator concentration significantly influenced the storage modulus G' of the hydrogel. For instance, a 20% concentration increment (10 to 12 wt. %) of $P(Bor)_5$-PEG-P$(Bor)_5$ resulted in 50% increase in G' value from 4203 to 6608 Pa.

TABLE 2

| | Polymer 1 | Amt. of Polymer 1 (wt. %) | Polymer 2 | Amt. of Polymer 2 (wt. %) | G' (Pa) | G" (Pa) |
|---|---|---|---|---|---|---|
| 1 | $P(Bor)_5$-PEG-P$(Bor)_5$ | 12 | — | — | 6608 ± 139 | 687 ± 73 |
| 2 | $P(Bor)_5$-PEG-P$(Bor)_5$ | 10 | — | — | 4203 ±163 | 629 ± 63 |
| 3 | $P(Bor)_5$-PEG-P$(Bor)_5$ | 7 | — | — | Does not gel | |
| 4 | $P(Bor)_5$-PEG-P$(Bor)_5$ | 10 | PEG-P$(Bor)_6$ | 2 | 3215 ± 139 | 558 ± 39 |
| 5 | $P(Bor)_5$-PEG-P$(Bor)_5$ | 10 | PEG-P$(Bor)_{12}$ | 2 | 2875 ± 119 | 463 ± 45 |
| 6 | $P(Bor)_5$-PEG-P$(Bor)_5$ | 8 | $P(Gu)_5$-PEG-P$(Gu)_5$ | 2 | 1804 ± 68 | 187 ± 17 |
| 6* | $P(Bor)_5$-PEG-P$(Bor)_5$ | 8 | $P(Gu)_5$-PEG-P$(Gu)_5$ | 2 | 2252 ± 78 | 335 ± 70 |
| 7 | $P(Bor)_5$-PEG-P$(Bor)_5$ | 8 | $P(Th)_5$-PEG-P$(Th)_5$ | 2 | 3672 ± 120 | 332 ± 29 |
| 8 | $P(Bor)_5$-PEG-P$(Bor)_5$ | 7 | $P(Gu)_5$-PEG-P$(Gu)_5$ | 3 | 695 ± 33 | 92 ± 7 |
| 8* | $P(Bor)_5$-PEG-P$(Bor)_5$ | 7 | $P(Gu)_5$-PEG-P$(Gu)_5$ | 3 | 1415 ± 29 | 108 ± 3 |
| 9 | $P(Bor)_5$-PEG-P$(Bor)_5$ | 7 | $P(Th)_5$-PEG-P$(Th)_5$ | 3 | 2071 ± 66 | 255 ± 11 |
| 10 | $P(Bor)_5$-PEG-P$(Bor)_5$ | 6 | $P(Gu)_5$-PEG-P$(Gu)_5$ | 4 | 54 ± 4 | 10 ± 5 |
| 11 | $P(Bor)_5$-PEG-P$(Bor)_5$ | 6 | $P(Th)_5$-PEG-P$(Th)_5$ | 4 | 871 ± 39 | 144 ± 10 |

Average values of G' and G" (Pa) measured between 10 to 25 rad/s.
*Contains BTZ-loaded micelles These hydrogels were too stiff to function as an injectable drug matrix through a 22 G needle. To reduce the storage modulus, $P(Bor)_5$-PEG-P$(Bor)_5$ was mixed with the boronic acid-functionalized diblock copolymers PEG-P$(Bor)_6$ and PEG-P$(Bor)_{12}$. The addition of the diblock copolymers significantly reduced the storage modulus, likely by the disruption in network formation by the addition of "dangling chain-ends." However, these gels were still not injectable. Mixing $P(Bor)_5$-PEG-P$(Bor)_5$ with the guanidinium- or thiouronium-containing triblock copolymers $P(Gua)_5$-PEG-P$(Gua)_5$ and $P(Th)_5$-PEG-P$(Th)_5$ led to great reduction in gel stiffness, conferring injectability to the hydrogels.

Micelle Preparation and Characterization

BTZ-loaded PEG-P$(Cat)_{12}$ micelles were prepared by a thin film-hydration method. Briefly, 5 mg of BTZ and 10 mg of PEG-P$(Cat)_{12}$ were dissolved in 7.5 mL of methanol via ultrasonication. Methanol was then evaporated under reduced pressure using a rotatory evaporator at 50° C., and a thin film was formed. HPLC grade water (5 mL) was added at 50° C. and sonicated for 30 min. To remove the insoluble residual drug, the mixture was centrifuged for 5 min at 4000 rpm, 25° C., followed by filtration using 0.22 μm nylon syringe filters.

The content of BTZ in PEG-P$(Cat)_{12}$ micelles was quantified by high performance liquid chromatography (HPLC, Waters 996 PDA detector, USA) at 280 nm. To determine the loading level of BTZ, the drug-loaded micelles were first freeze-dried and then re-dissolved in mobile phase consisting of acetonitrile, water and THF in the volume ratio of 65:30:5. The drug loading level was calculated based on the ratio of the amount of drug encapsulated in the micelles to the amount of drug-loaded micelles. Encapsulation efficiency and loading level were 57±6% and 50±2%, respectively. The particle size and polydispersity index (PDI) of the blank and drug-loaded micelles were measured to be (42 nm, 0.26) and (62 nm, 0.11), respectively. The PDI of drug-loaded micelles was much smaller compared to blank micelles, suggesting formation of a more compact micellar core after drug loading.

The rheological analysis of the hydrogels was performed on an ARES-G2 rheometer (TA Instruments, USA) under controlled strain of 2.0% and a frequency scan of 1.0 to 100 rad/s.

To minimize any interference to the morphological analysis, the hydrogels were cryo-fixed by transferring the sample into a chamber filled with liquid nitrogen. Freeze-drying process lasting 24 h was then followed. The morphology of the gel was observed using a scanning electron microscope (SEM) (Jeol JSM-7400F, Japan).

In Vitro Drug Release

BTZ release from the BTZ-loaded micelles and BTZ-loaded micelle/hydrogel composite was studied using the dialysis method. The micelles or the gel (500 μL) was transferred to a dialysis membrane tube with MWCO of 1000 Da (Spectrum Laboratories, USA). The tubes were immersed in 10 mL of the release medium of different pH, i.e. PBS buffer (100 mM, pH 7.4 or 5.8) to maintain a constant sink condition. This was kept shaking on an orbital shaker at 100 rpm at 37° C. At various time intervals, the release medium was removed and replaced with fresh medium. Samples of the release medium were collected and diluted 10 times using the HPLC mobile phase and bortezomib content was analyzed using HPLC at 280 nm.

Figure 1:
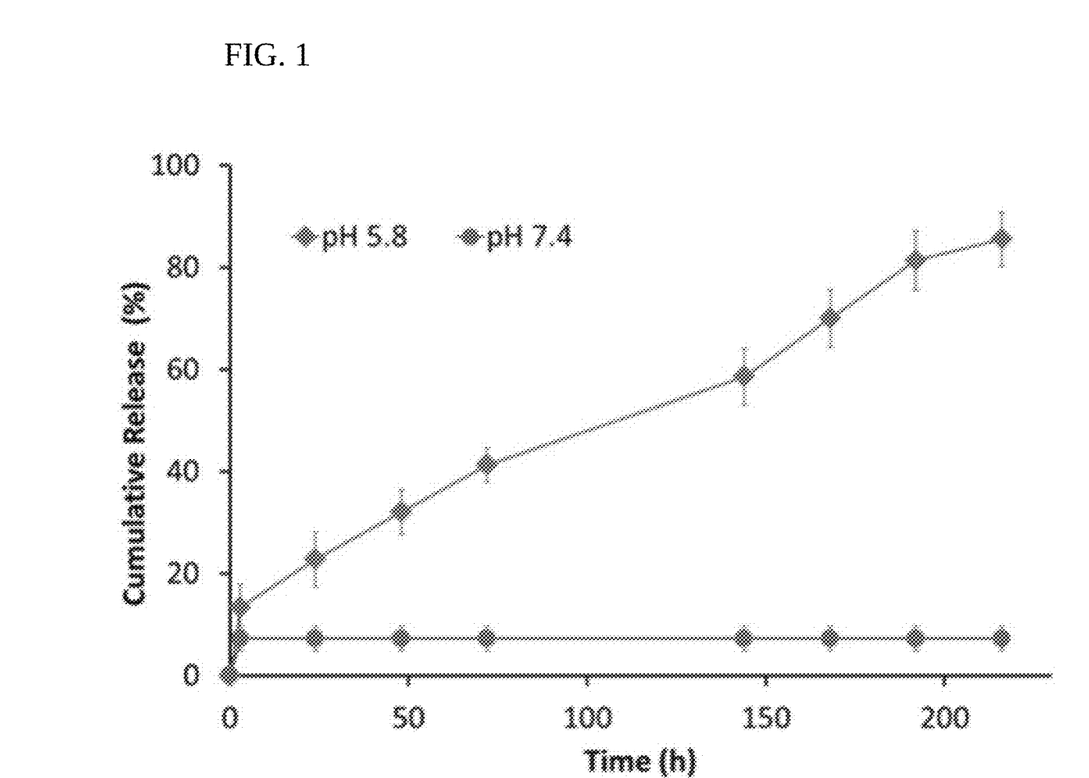
FIG. 1 shows a plot of the cumulative release of BTZ from BTZ-loaded micelles of hydrogels according to embodiments of the invention.

As shown in FIG. 1, at pH 7.4, the release of BTZ from the micelle/hydrogel composite remained low at 7% throughout the experiment, while the release was significantly higher at pH 5.8. In the acidic environment, drug release was gradual and could be sustained for 9 days with ~85% of BTZ being released cumulatively. Several studies have reported the pH-sensitive dissociation of boronate esters, where at acidic pH, the hydrolysis of the boronate ester bond takes place, thereby resulting in the release of the encapsulated BTZ. The pH sensitivity of the micelles was further verified in a separate experiment where the drug release profiles of BTZ-loaded micelles were studied. BTZ release from the micelles was much faster at acidic pH compared to physiological pH 7.4. Such property confers good advantage for the micelle/hydrogel composite to function as a drug reservoir for cancer treatment as the release of BTZ from the micelles will be limited under the normal physiological pH, while the dissociation of boronate ester and BTZ release will be encouraged under the endolysosomal pH following endocytosis.

Cytotoxicity Test

Human multiple myeloma (MM.1S) cells were seeded at a density of $10 \times 10^3$ cells per well onto a 96 well plate and incubated overnight at 37° C. On the day of treatment, the medium was removed and 90 µl of RPMI was added to each well. Following this, 10 µL of the hydrogels or micelles-containing hydrogels were added to the cells. The plate was then incubated for another 48 h at 37° C. Reagents from the CellTiter 96® AQueous One Solution Cell Proliferation Assay Kit (Promega, USA) and RPMI were then mixed at a volume ratio of 1:4 and 100 µL of this mixture was then added to each well and the cells were left to incubate in the dark at 37° C. for 2 h. Untreated cells were then used as the control. Subsequently, the absorbance at 490 nm was measured and the readings were then expressed as a percentage of the cell viability of the control.

Treatment using samples that do not contain BTZ, i.e. blank (B7+G3)hydrogel and PEG-P(Cat)$_{12}$ micelles showed almost negligible toxicity on MM.1S cells where cell viability remain high at >90%. The reductions in cell viabilities were similar between micelles and micelle/hydrogel composites containing BTZ-loaded and free BTZ formulations, showing that BTZ could be released from the matrices and the drug remain functional after the encapsulation procedure.

Figure 2:
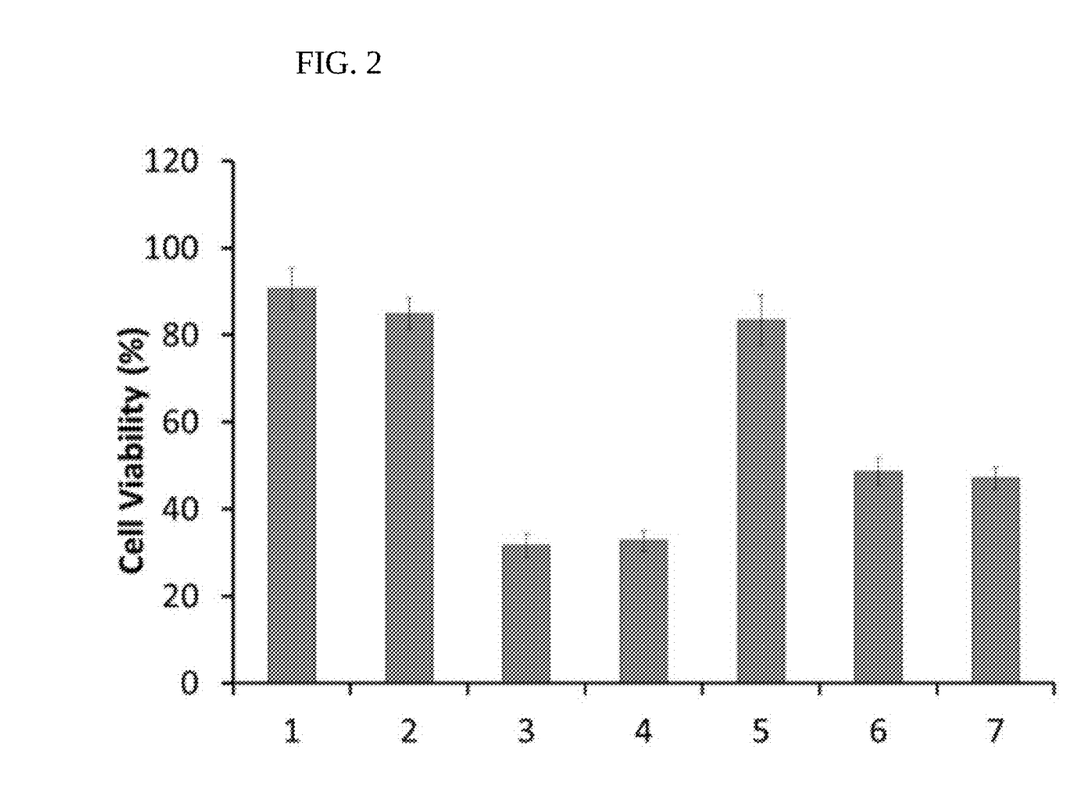
FIG. 2 shows a plot of the effect on cell viability of blank hydrogels and micelles as compared to BTZ-loaded micelles according to embodiments of the invention.

Table 3 below shows the compositions of various samples tested for cytotoxic effects. The effect of each of these samples on cell viability is shown in FIG. 2. As can be seen, blank micelles and the hydrogels themselves had little or no effect on cell viability, while BTZ-loaded micelles and free BTZ, alone or combined with the hydrogels, exhibited a marked effect on cell viability.

TABLE 3

| Sample | Component 1 | Component 2 |
| --- | --- | --- |
| 1 | Gel | — |
| 2 | Gel | Blank Micelle |
| 3 | Gel | BTZ-loaded Micelle |
| 4 | Gel | Free BTZ |
| 5 | — | Blank Micelle |
| 6 | — | BTZ-loaded Micelle |
| 7 | — | Free BTZ |

Animal Studies

All animal studies were permitted by the Biological Resource Centre of Singapore with approved protocol from the Institutional Animal Care and Use Committee (IACUC). CB-17 severe combined immunodeficient (SCID) mice were subcutaneously inoculated with $5 \times 10^6$ MM.1S cells in 200 µL 1:1 mixture of serum-free RPMI-1640 medium and matrigel.

Biodistribution of Micelles

To simulate the in vivo biodistribution of the micelles, a near-infrared fluorophore DiR was loaded into the PEG-P(Cat)$_{12}$ micelles by a solvent evaporation technique. Briefly, 2 mg of DiR and 10 mg of PEG-P(Cat)$_{12}$ were dissolved in 7.5 mL of methanol via ultrasonication. Methanol was then evaporated under reduced pressure using a rotatory evaporator at 50° C., and a film was formed. HPLC grade water (5 mL) was added at 50° C. and sonicated for 30 min. To remove the insoluble residual drug, the mixture was centrifuged for 5 min at 4000 rpm, 25° C., followed by filtration using 0.22 µm nylon syringe filters. To determine the loading level of DiR, the dye-loaded micelles were dissolved in DMSO and absorbance was measured against a standard calibration curve of free dye dissolved in the same solvent at 759 nm wavelength.

Three weeks after inoculation (when the tumor volume was around 300 mm$^3$), the tumor-bearing mice were divided into 4 groups and administrated with 0.35 mg/kg DiR in different formulations: (1) hydrogel, (2) PEG-(Cat)$_{12}$ micelle solution, (3) free DiR in hydrogel and (4) free DiR solution, injected subcutaneously at approximately 1 cm away from the tumor site. Anesthetic animals were placed on an animal plate heated to 37° C. The near-infrared fluorescence was imaged using the ICG filter pairs and exposure time was set to 1 s. Scans were performed at 1, 2, 3, 7, 10, 14, 17 and 21 days post administration. The mice were sacrificed on Day 13 and organs involved in drug clearance and metabolism as well as tumor tissue were excised and imaged using IVIS (Caliper Life Science, USA).

In Vitro Anti-Cancer Efficacy

Three weeks after inoculation (when the tumor volume was around 300 mm$^3$), the tumor-bearing mice were randomly divided into five groups with 7-10 mice per group: (1) Untreated control, (2) blank PEG-P(Cat)$_{12}$ micelle solution (150 µL), (3) blank hydrogel (150 µL), (4) bortezomib-loaded micelle solution (0.8 mg/kg bortezomib, 150 µL), (5) bortezomib-loaded micelle/hydrogel composite (0.8 mg/kg bortezomib, 150 µL). Injections were carried out subcutaneously at ~1 cm away from the tumor sites. All mice were injected only once on the first day of treatment (Day 0).

Mice were monitored for body weight and tumor volume by caliper measurements twice a week. Tumor volume was estimated using the following formula: L×W²/2, where L and W are the major and minor diameters respectively. Two-tailed Student's t test was used to determine statistical differences in tumor volume and P≤0.05 was considered to show a statistical significance.

Figure 3:
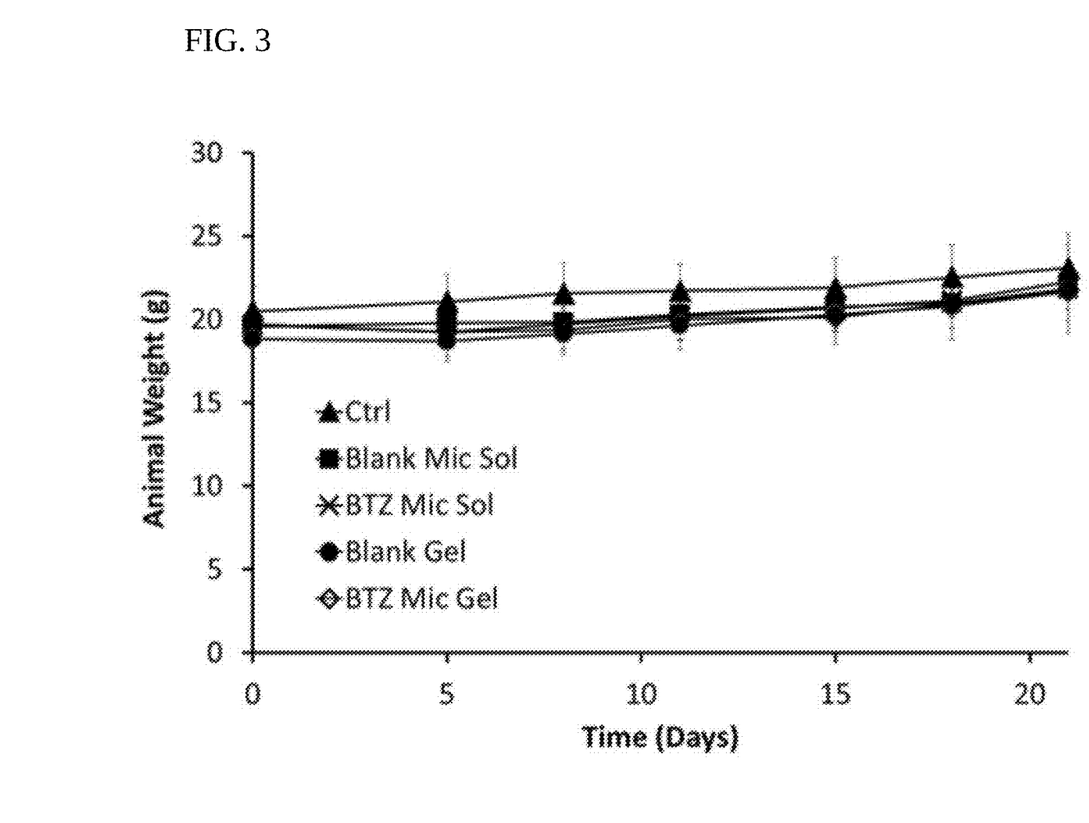
FIG. 3 shows a plot of the change in weight of mice treated according to embodiments of the invention.

No clinical signs of toxicity such as weight loss, reduced appetite or lethargy were observed for all mice during the course of treatment, indicating good tolerance to all treatment conditions. FIG. 3 shows a plot of animal weight over time for each of these groups.

Figure 4:
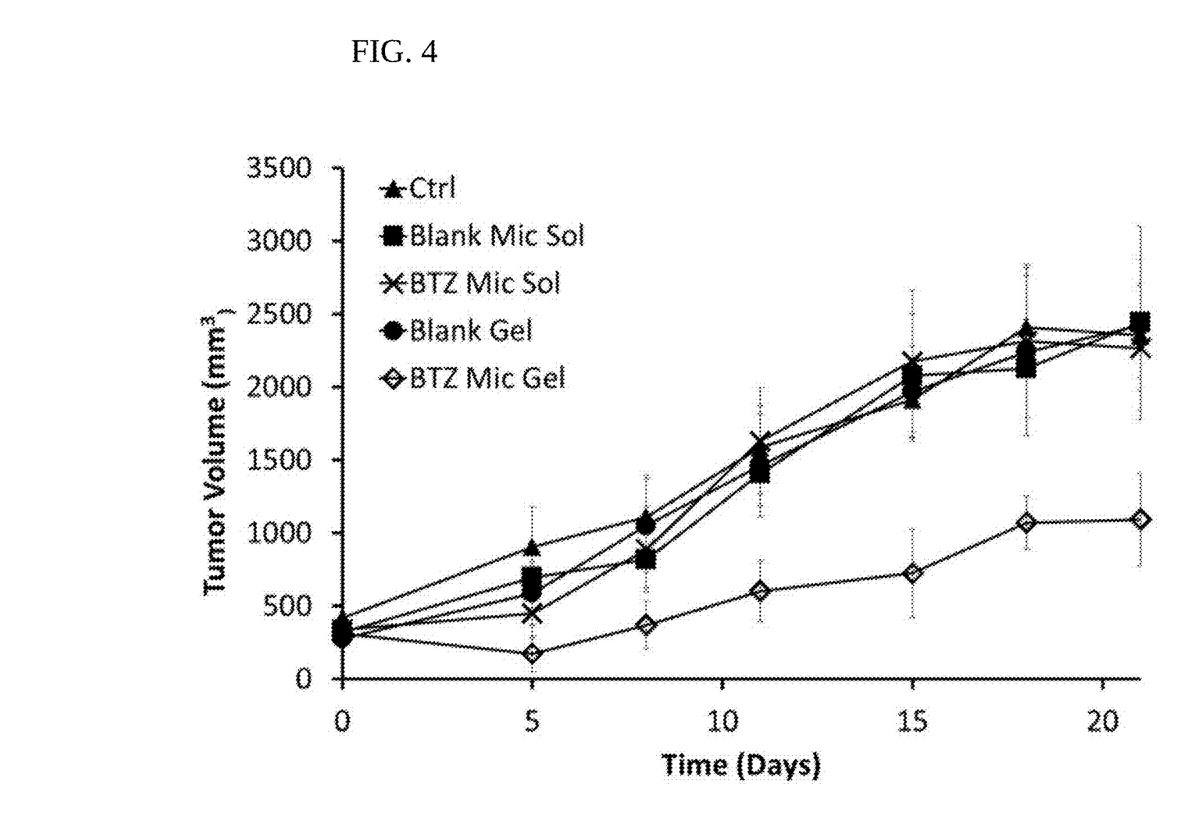
FIG. 4 shows a plot of the effect of treatment according to embodiments of the invention on tumor volume in mice.

Large differences in tumor growth rates were observed in mice that were treated with the solution and hydrogel formulations. FIG. 4 shows tumor volume over time for each group.

As can be seen in FIG. 4, mice that were treated with BTZ-loaded micelle solution had similar tumor progression profile as the control group, demonstrating that the solution formulation was unable to exert therapeutic effects on the tumors at the given dose. Notably, administration of the BTZ-loaded micelle/(B7+G3)hydrogel resulted in significant delay in tumor progression (P<0.001) compared to other treatment groups.

Figure 5:
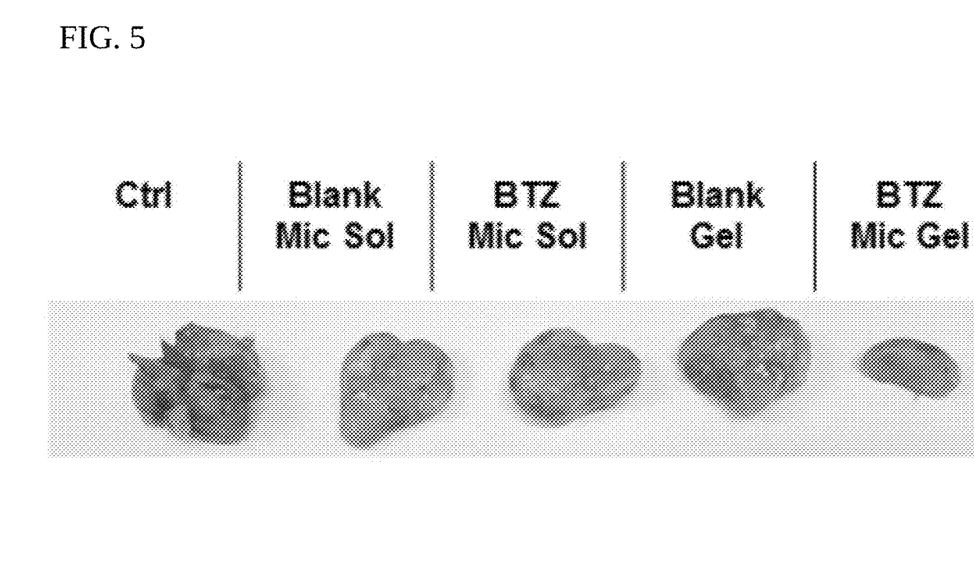
FIG. 5 shows a photograph of tumors excised from mice following various treatments, including treatments according to embodiments of the invention.

Furthermore, the group that was treated with BTZ-loaded mica e/(B7+G3) hydrogel did not display noticeable increase in tumor size for the first 8 days post injection (P>0.01) and only showed tumor size increment by 11 days post injection and onwards. This was likely due to the diffusion barrier that the hydrogel matrix provided which helped to prolong the release of BTZ-loaded micelles into the circulation and tumor site. At the end of the experiment, the mice were sacrificed and tumors were resected. Tumors that were removed from mice treated with BTZ-loaded micelle/(B7+G3)hydrogel composite were much smaller compared to other treatment groups, as can be seen in the photograph of FIG. 5.

In sum, embodiments of the invention provide a biodegradable and injectable hydrogels formed via ionic coacervation between phenylboronic acid-functionalized polycarbonate and PEG ABA triblock copolymers with cationic guanidine- and thiouronium-functionalized polycarbonate and PEG ABA triblock copolymers. These hydrogels were developed as a local delivery matrix for sustained release of the anticancer drug bortezomib-loaded micelles.

BTZ was encapsulated in catechol-functionalized polycarbonate micelles via pH-sensitive boronate ester bond formed between catechol and phenylboronic acid group in BTZ, and these micelles were incorporated into the hydrogels to form BTZ-loaded micelle/hydrogel composites. The in vitro release of BTZ from the composite gel was pH dependent, with sustained gradual release of ~85% over 9 days in acidic environment while remaining low at 7% at physiological pH.

In vivo studies performed on multiple myeloma MM.1S-bearing mice slowed large difference in tumor growth rates in mice that were treated with solution and hydrogel formulations. Anti-tumor efficacy is significantly enhanced using a single subcutaneous injection of bortezomib-loaded micelle hydrogel composite as compared to bortezomib-loaded micelle solution. These results suggest that the incorporation of drug-loaded micelles into hydrogels hold great promise for subcutaneous and sustained delivery of anticancer drugs with minimal invasive procedure.

The terminology used herein is for the purpose of describing particular embodiments only and is not intended to be limiting of the invention. As used here, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A hydrogel composition comprising:
 a first ABA triblock copolymer having negatively charged A blocks, wherein the first ABA triblock copolymer is a phenylboronic acid-functionalized polycarbonate/poly(ethylene glycol) (PEG) ABA triblock copolymer; and
 a second ABA triblock copolymer having positively charged A blocks.

2. The hydrogel composition of claim 1, wherein the first ABA triblock copolymer has the structure of formula I:

(formula I)

wherein m is between 1 and 10 and PEG$_{10K}$ is 10 kDa poly(ethylene glycol).

3. The hydrogel composition of claim 2, wherein m is 5.

4. The hydrogel composition of claim 1, wherein the second ABA triblock copolymer includes A blocks containing either guanidine or thiouronium.

5. The hydrogel composition of claim 4, wherein the second ABA triblock copolymer has the structure of formula II:

(formula II)

wherein x is between 1 and 10, n is 227, and TFA is trifluoroacetic acid.

6. The hydrogel composition of claim 5, wherein x is 5.

7. The hydrogel composition of claim 4, wherein the second ABA triblock copolymer has the structure of formula III:

(formula III)

wherein m is between 1 and 10 and n is 227.

8. The hydrogel composition of claim 7, wherein m is 5.

9. A micellar particle comprising:
a hydrogel composition comprising:
  a first ABA triblock copolymer having negatively charged A blocks, wherein the first ABA triblock copolymer is a phenylboronic acid-functionalized polycarbonate/poly(ethylene glycol) (PEG) ABA triblock copolymer; and
  a second ABA triblock copolymer having positively charged A blocks; and
at least one agent for delivery within the hydrogel composition.

10. The micellar particle of claim 9, wherein:
the first ABA triblock copolymer is a phenylboronic acid-functionalized polycarbonate/poly(ethylene glycol) (PEG) ABA triblock copolymer has the structure of formula I:

(formula I)

wherein m is between 1 and 10 and PEG$_{10K}$ is 10 kDa poly(ethylene glycol); and
the second ABA triblock copolymer has the structure of formula II or the structure of formula III:

(formula II)

wherein x is between 1 and 10, n is 227, and TFA is trifluoroacetic acid, (formula III)

wherein m is between 1 and 10 and n is 227.

* * * * *